United States Patent
Bräunlich et al.

(10) Patent No.: US 6,677,372 B2
(45) Date of Patent: *Jan. 13, 2004

(54) N-(3-BENZOFURANYL)UREA-DERIVATIVES

(75) Inventors: Gabriele Bräunlich, Wuppertal (DE); Rüdiger Fischer, Köln (DE); Mazen Es-Sayed, Wuppertal (DE); Rolf Henning, Wachtberg (DE); Michael Sperzel, Wuppertal (DE); Karl-Heinz Schlemmer, Wuppertal (DE); Ulrich Nielsch, Wuppertal (DE); Stephen Tudhope, Windsor Berkshire (GB); Graham Sturton, Bray Maidenhead (GB); Trevor S. Abram, Marlow Buckinghamshire (GB); Mary F. Fitzgerald, Begbroke Oxford (GB)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/154,743

(22) Filed: May 24, 2002

(65) Prior Publication Data

US 2003/0109578 A1 Jun. 12, 2003

Related U.S. Application Data

(62) Division of application No. 09/316,536, filed on May 21, 1999, now Pat. No. 6,399,657, which is a continuation of application No. 08/610,319, filed on Mar. 4, 1996, now abandoned.

(51) Int. Cl.$^7$ .................. A61K 31/343; A61P 29/00; C07D 307/82
(52) U.S. Cl. .................. 514/470; 549/467
(58) Field of Search .................. 549/467; 514/470

(56) References Cited

U.S. PATENT DOCUMENTS

| | | | |
|---|---|---|---|
| 4,663,347 A | 5/1987 | Atkinson et al. | 514/467 |
| 4,822,803 A | 4/1989 | Atkinson et al. | 514/320 |
| 4,933,351 A | 6/1990 | Atkinson et al. | 514/320 |

FOREIGN PATENT DOCUMENTS

| | | |
|---|---|---|
| EP | 0 069 521 | 1/1983 |
| EP | 0 146 243 | 6/1985 |

OTHER PUBLICATIONS

Nagata et al., *Int. Arch. Allergy Immunol.*, 97: 194–199 (1992).
Schudt, *Biochem. Pharmacol.*, 42: 153–162 (1991).
Schneider et al. *Eur. J. Biochem.*, 127: 105–115 (1986).
Souness et al., *Biochem. J.*, 291: 389–395 (1993).

*Primary Examiner*—Patricia L. Morris
(74) *Attorney, Agent, or Firm*—Norris McLaughlin & Marcus

(57) ABSTRACT

N-(3-benzofuranyl)urea-derivatives are prepared by reacting of 3-amino-substituted benzofuranes with appropriate substituted isocyanates or isothiocyanates. The N(3-benzofuranyl)urea-derivatives can be used as active ingredients in medicaments particularly for the treatment of acute and chronic inflammatory processes.

11 Claims, No Drawings

N-(3-BENZOFURANYL)UREA-DERIVATIVES

This application is a divisional of U.S. Ser No. 09/316,536, filed May 21, 1999, now U.S. Pat. No. 6,399,657, which is a continuation of U.S. Ser. No. 08/610,319, filed Mar. 4, 1996, which is abandoned.

The invention relates to N-(3-benzofuranyl)urea-derivatives, processes for their preparation and their use in medicaments.

It is known that the NADPH oxidase of phagocytes is the physiological source to the superoxide radical anion and reactive oxygen species derived therefrom which are important in the defence against pathogens. Moreover, both inflammatory (e.g. TNFα, IL-1 or IL-6) and anti-inflammatory cytokines (e.g. IL-10) play a pivotal role in host defence mechanism. Uncontrolled production of inflammatory mediators can lead to acute or chronic inflammation, auto immune diseases, tissue damage, multi-organ failure and to death. It is additionally known that elevation of phagocyte cyclic AMP leads to inhibition of oxygen radical production and that this cell function is more sensitive than others such as aggregation or enzyme release.

Benzofuran- and benzothiophene derivatives having lipoxygenase-inhibiting action are described in the publication EP 146 243.

The invention relates to N-(3-benzofuranyl)urea-derivatives of the general formula (I)

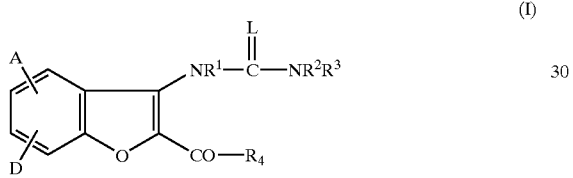

in which
A and D are identical or different and represent hydrogen, straight-chain or branched acyl or alkoxycarbonyl, each having up to 6 carbon atoms, or straight-chain or branched alkyl having up to 6 carbon atoms, which is optionally substituted by carboxyl or alkoxycarbonyl having up to 6 carbon atoms, phenoxy or benzoyl,
or represent halogen, carboxyl, cyano, nitro, trifluoromethyl, trifluoromethoxy or a group of a formula $-OR^5$, $-S(O)_aR^6$, $-(O-CH_2-CO)_b-NR^7R^8$, $-CO-NR^9R^{10}$, $-SO_2-NR^{11}R^{12}$ or $-NH-SO_2R^{13}$, in which
$R^5$, $R^6$, $R^8$, $R^9$, $R^{10}$, $R^{11}$ and $R^{12}$ are identical or different and denote hydrogen, cycloalkyl having 3 to 6 carbon atoms, benzyl or a 5 to 7-membered saturated or unsaturated heterocycle having up to 3 heteroatoms from the series comprising N, S and O and to which a phenyl ring can be fused and which is optionally substituted by identical or different substituents from the series comprising halogen, cyano, nitro or by a straight-chain or branched alkyl having up to 6 carbon atoms or
denote straight-chain or branched alkyl, alkenyl or acyl each having up to 8 carbon atoms, or
denote phenyl, which is optionally monosubstituted to disubstituted by identical or different substituents from the series comprising nitro, halogen, carboxy or straight-chain or branched alkoxycarbonyl having up to 6 carbon atoms, or
$R^5$ denotes a hydroxyl protecting group or straight-chain or branched alkoxycarbonyl having up to 6 carbon atoms, or
denotes straight-chain or branched alkyl having up to 8 carbon atoms, which is substituted by carboxyl, hydroxyl, straight-chain or branched acyl or alkoxycarbonyl each having up to 6 carbon atoms, phenoxy, benzoyl or by a 5 to 7-membered unsaturated heterocycle having up to 3 hetero atoms from the series comprising N, S and/or O, which is optionally substituted by halogen, cyano, nitro or by straight-chain or branched alkyl having up to 6 carbon atoms or
$R^5$ denotes a group of a formula $SO_2R^{14}$, in which $R^{14}$ denotes phenyl, trifluormethyl or straight-chain or branched alkyl having up to 4 carbon atoms,
a denotes a number 0, 1 or 2,
b denotes a number 0 or 1,
$R^7$ denotes hydrogen or a straight-chain or branched alkyl having up to 4 carbon atoms,
$R^{13}$ denotes aryl having up 6 to 10 carbon atoms, trifluoromethyl or straight-chain or branched alkyl having up to 6 carbon atoms,
$R^1$ represents hydrogen, straight-chain or branched alkyl having up to 6 carbon atoms, an aminoprotecting group or a group of the formula $-CO-R^{15}$, in which
$R^{15}$ denotes hydroxyl, straight chain or branched alkoxycarbonyl having up to 6 carbon atoms, cycloalkyl having up 3 to 6 carbon atoms, pyridyl, pyrrolidinyl or straight chain or branched alkyl having up to 8 carbon atoms, which is optionally substituted by halogen, carboxyl or straight chain or branched alkoxycarbonyl having up to 6 carbon atoms, or
denotes phenyl, which is optionally substituted by hydroxyl, carboxyl or straight chain or branched alkoxy or alkoxycarbonyl each having up to 6 carbon atoms,
L represents an oxygen or sulfur atom,
$R^2$ and $R^3$ are identical or different and represent hydrogen, cycloalkyl having up to 6 carbon atoms, straight chain or branched alkyl, alkoxycarbonyl or alkenyl each having up to 8 carbon atoms, or
represent benzoyl or aryl having 6 to 10 carbon atoms, which are optionally monosubstituted to trisubstituted by identical or different substituents from the series comprising halogen, cyano, nitro, carboxyl, straight-chain or branched alkyl, alkoxy, alkoxycarbonyl or acyl each having up to 6 carbon atoms, or
$R^2$ and $R^3$ together with the nitrogen atom form a 5- to 7-membered saturated heterocycle optionally having a further O atom, and
$R^4$ represents phenyl, which is optionally monosubstituted to trisubstituted by identical or different substituents from the series comprising hydroxyl, thiophenyl, cycloalkyl having up to 3 to 6 carbon atoms, halogen, nitro, tetrazolyl, thiazolyl, furanyl, pyridyl, trifluoromethyl, difluoromethyl, cyano, carboxyl, straight-chain or branched alkyl, alkoxy, alkoxycarbonyl or acyl each having up to 8 carbon atoms, or
phenyl is optionally substituted by phenyl, which is optionally monosubstituted to disubstituted by halogen, or
by a group of a formula $-NR^{16}R^{17}$, $-SR^{18}$, $SO_2R^{19}$ or $-O-SO_2R^{20}$, in which
$R^{16}$ and $R^{17}$ have the abovementioned meaning of $R^7$ and $R^8$ and are identical or different to the latter, or $R^{16}$ denotes hydrogen, and $R^{17}$ denotes straight-chain or branched acyl having up to 6 carbon atoms, $R^{18}$ denotes hydrogen or straight-chain or branched alkyl having-up to 6 carbon atoms, $R^{19}$ and $R^{20}$ are identical or different and represent straight-chain or branched alkyl having up to 6 carbon atoms, benzyl or phenyl, and salts thereof.

The N-(3-benzofuranyl)urea-derivatives according to the invention can also be present in the form of their salts. In general, salts with organic or inorganic bases or acids may be mentioned here.

Physiologically acceptable salts are preferred in the context of the present invention. Physiologically acceptable salts of the N-(3-benzofuranyl)urea-derivatives can be metal or ammonium salts of the substances according to the invention, which contain a free carboxylic group. Those which are particularly preferred are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

Physiologically acceptable salts can also be salts of the compounds according to the invention with inorganic or organic acids. Preferred salts here are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, ethanesulphonic acid, benzenesulphonic acid, toluenesulphonic acid or naphthalenedisulphonic acid.

The compounds according to the invention can exist in stereoisomeric forms which either behave as image and mirror image (enantiomers), or which do not behave as image and mirror image (diastereomers). The invention relates both to the antipodes and to the racemate forms, as well as the diastereomer mixtures. The racemate forms, like the diastereomers, can be separated into the stereoisomerically uniform constituents in a known manner.

Heterocycle in general represents a 5- to 7-membered saturated or unsaturated, preferably 5- to 6-membered, saturated or unsaturated ring which can contain up to 3 oxygen, sulphur and/or nitrogen atoms as heteroatoms and to which further aromatic ring can be fused.

The following are mentioned as preferred: thienyl, furyl, pyrrolyl, pyridyl, pyrimidyl, pyrazinyl, pyridazinyl, quinolyl, isoquinolyl, quinazolyl, quinoxazolyl, cinnolyl, thiazolyl, dihydrothiazolyl, benzothiaazolyl, isothiazolyl, benzisothiazolyl, oxazolyl, benzoxazolyl, isoxazolyl, imidazolyl, benzimidazolyl, indolyl, morpholinyl, pyrrolidinyl, piperidyl, piperazinyl, oxazolyl, oxazolinyl or triazolyl.

Amino protective group in the context of the above mentioned definition in general represents a protective group from the series comprising: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tertbutoxycarbonyl, allyloxycarbonyl, vinyloxycarbonyl, 2-nitrobenzyloxycarbonyl, 3,4,5-trimethoxybenzyloxycarbonyl, cyclohexoxycarbonyl, 1,1-dimethylethoxycarbonyl, adamantylcarbonyl, phthaloyl, 2,2,2-trichlorethoxycarbonyl, 2,2,2-trichlor-tertbutoxycarbonyl, menthyloxycarbonyl, phenoxycarbonyl, 4-nitrophenoxycarbonyl, fluorenyl-9-methoxycarbonyl, formyl, acetyl, propionyl, pivaloyl, 2-chloracetyl, 2-bromacetyl, 2,2,2-trifluoracetyl, 2,2,2-trichloracetyl, benzoyl, 4-chlorbenzoyl, 4-brombenzoyl, 4-nitrobenzoyl, phthalimido, isovaleroyl oder benzyloxymethylen, 4-nitrobenzyl, 2,4-dinitrobenzyl or 4-nitrophenyl.

Preferred compounds of the general formula (I) are those in which

A and D are identical or different and represent hydrogen, straight-chain and branched acyl or alkoxycarbonyl each having up to 5 carbon atoms or straight-chain or branched alkyl having up to 4 carbon atoms wich is optionally substituted by carboxyl, hydroxyl, alkoxycarbonyl having up to 5 carbon atoms, phenoxy or benzoyl, or represent fluorine, chlorine, bromine, nitro, trifluoromethyl or a group of a formula $-OR^5$, $-S(O)_a-R^6$, $(O-CH_2-CO)_b-NR^7R^8$, $-CO-NR^9R^{10}$, $-SO-NR^{11}R^{12}$ or $-NH-SO_2-R^{13}$, in which $R^5$, $R^6$, $R^8$, $R^9$, $R^{10}$, $R^{11}$ and $R^{12}$ are identical or different and denote hydrogen, cyclopropyl, cyclopentyl, cyclohexyl, chinolyl, pyridyl, imidazolyl, 1,3-thiazolyl or thienyl, which are optionally substituted by identical or different substituents from the series comprising fluorine, chlorine, bromine, iodine, cyano, nitro or by a straight-chain or branched alkyl having up to 5 carbon atoms, denote straight-chain or branched alkyl, alkenyl or acyl each having up to 6 carbon atoms, or denote phenyl, which is optionally monosubstituted to disubstituted by identical or different substituents from the series comprising nitro, fluorine, chlorine, bromine, iodine, carboxyl or straight-chain or branched alkoxycarbonyl having up to 5 carbon atoms, or $R^5$ denotes benzyl, acetyl or tetrahydropyranyl or straight chain or branched alkoxycarbonyl having up to 4 carbon atoms, denotes straight-chain or branched alkyl having up to 6 carbon atoms, which is substituted by carboxyl, hydroxyl, straight-chain or branched acyl or alkoxycarbonyl each having up to 4 carbon atoms, phenoxyl, benzoyl or by pyridyl, imidazolyl, thienyl or furyl, which are optionally substituted by fluorine, chlorine, bromine, cyano, nitro or by straight-chain or branched alkyl having up to 4 carbon atoms, or $R^5$ denotes a group of a formula $-SO_2-R^{14}$, in which $R^{14}$ denotes phenyl, trifluormethyl or straight-chain or branched alkyl having up to 3 carbon atoms, a denotes a number 0, 1 or 2, b denotes a number 0 or 1, $R^7$ denotes hydrogen or a straight-chain or branched alkyl having up to 3 carbon atoms, $R^{13}$ denotes phenyl, trifluormethyl or straight-chain or branched alkyl having up to 3 carbon atoms, $R^1$ represents hydrogen, straight-chain or branched alkyl having up to 4 carbon atoms, tertbutoxycarbonyl or a group of the formula $-CO-R^{15}$ in which $R^{15}$ denotes hydroxyl, straight chain or branched alkoxycarbonyl having up to 4 carbon atoms, cyclopentyl, cyclohexyl, pyridyl, pyrrolidinyl or straight chain or branched alkyl having up to 5 carbon atoms, which is optionally substituted by fluorine, chlorine, bromine, carboxyl or straight chain or branched alkoxycarbonyl having up to 4 carbon atoms, or denotes phenyl, which is optionally substituted by hydroxyl, carboxyl or straight chain or branched alkoxy or alkoxycarbonyl each having up to 4 carbon atoms, L represents an oxygen or sulfur atom, $R^2$ and $R^3$ are identical or different and represent hydrogen, cyclobutyl, cyclopentyl, cyclohexyl or straight-chain or branched alkyl, alkoxycarbonyl or alkenyl each having up to 6 carbon atoms, or represent benzoyl or phenyl, which are optionally monosubstituted to trisubstituted by identical or different substituents from the series comprising fluorine, chlorine, bromine, iodine, carboxyl, cyano, nitro or by a straight-chain or branched alkyl, alkoxy or alkoxycarbonyl each having up to 5 carbon atoms, or $R^2$ and $R^3$ together with the nitrogen atom form a pyrrolidinyl, piperidinyl or morpholinyl ring, and $R^4$ represents phenyl, which is optionally monosubstituted to trisubstituted by identical or different substituents from the series comprising hydroxyl, thiophenyl, cyclopentyl, cyclohexyl, fluorine, chlorine, bromine, iodine, nitro, tetrazolyl, thiazolyl, furanyl, pyridyl, trifluoromethyl, difluoromethyl, cyano, carboxyl, straight-chain or branched alkyl, alkoxy, alkoxycarbonyl or acyl each having up to 6 carbon atoms, or phenyl is optionally substituted by phenyl, which is optionally monosubstituted to disubstituted by fluorine, chlorine or bromine, and salts thereof.

Particularly preferred compounds of the general formula (I) are those in which

A and D are identical or different and represent hydrogen, straight-chain or branched acyl or alkoxycarbonyl each having up to 4 carbon atoms, or straight-chain or branched alkyl having up to 3 carbon atoms, which is optionally substituted by carboxyl or alkoxycarbonyl having up to 4 carbon atoms, phenoxy or benzoyl, or represent fluorine, chlorine, bromine, nitro, cyano, trifluoromethyl, trifluormethoxy, or a group of a formula —$OR^5$, —$S(O)_aR^6$, —$(O-CH_2-CO)_b-NR^7R^8$, —$CO-NR^9R^{10}$, —$SO_2-NR^{11}R^{12}$ or —$NH-SO_2R^{13}$, in which $R^5$, $R^6$, $R^8$, $R^9$, $R^{10}$, $R^{11}$ and $R^{12}$ are identical and denote hydrogen, cyclopropyl, cyclopentyl, cyclohexyl, chinolyl, pyridyl, imidazolyl, 1,3-thiazolyl or thienyl, which are optionally substituted by identical or different substitutents from the series comprising fluorine, chlorine, bromine, iodine, cyano, nitro or by a straight-chain or branched alkyl having up to 3 carbon atoms, denote straight-chain or branched alkyl, alkenyl or acyl each having up to 3 carbon atoms, or denote phenyl, which is optionally monosubstituted to disubstituted by identical or different substituents from the series comprising nitro, fluorine, chlorine, bromine, iodine, carboxyl or straight-chain or branched alkoxycarbonyl having up to 3 carbon atoms, or $R^5$ denotes benzyl, acetyl or tetrahydropyranyl or straight-chain or branched alkoxycarbonyl having up to 3 carbon atoms, denotes straight-chain or branched alkyl having up to 4 carbon atoms, which is substituted by carboxyl, hydroxyl, straight-chain or branched acyl or alkoxycarbonyl each having up to 3 carbon atoms, phenoxy, benzoyl or by pyridyl, imidazolyl or thienyl, or $R^5$ denotes a group of a formula —$SO_2-R^{14}$, in which $R^{14}$ denotes phenyl, trifluormethyl or methyl, a denotes a number 0, 1 or 2, b denotes a number 0 or 1, $R^7$ denotes hydrogen, methyl or ethyl, $R^{13}$ denotes phenyl, trifluoromethyl or methyl, $R^1$ represents hydrogen or straight-chain or branched alkyl having up to 3 carbon atoms or a group of the formula —$CO-R^{15}$, in which $R^{15}$ denotes hydroxyl, straight chain or branched alkoxycarbonyl having up to 3 carbon atoms, cyclopentyl, cyclohexyl, pyridyl, pyrrolidinyl or straight chain or branched alkyl having up to 4 carbon atoms, which is optionally substituted by fluorine, chlorine, bromine, carboxyl or straight chain or branched alkoxycarbonyl having up to 3 carbon atoms, or denotes phenyl, which is optionally substituted by hydroxyl, carboxyl or straight chain or branched alkoxy or alkoxycarbonyl each having up to 3 carbon atoms, L represents an oxygen or sulfur atom, $R^2$ and $R^3$ are identical or different and represent hydrogen, cyclobutyl, cyclopentyl, cyclohexyl or straight-chain or branched alkyl, alkoxycarbonyl or alkenyl each having up to 5 carbon atoms, or represent benzoyl or phenyl, which are optionally monosubstituted to trisubstituted by identical or different substituents from the series comprising fluorine, chlorine, bromine, iodine, carboxy, cyano, nitro or by a straight-chain or branched alkyl, alkoxy or alkoxycarbonyl each having up to 3 carbon atoms, or $R^2$ and $R^3$ together with the nitrogen atom form a pyrrolidinyl ring, and $R^4$ represents phenyl, which is optionally monosubstituted to trisubstituted by identical or different substituents from the series comprising hydroxyl, thiophenyl, cyclopentyl, cyclohexyl, fluorine, chlorine, bromine, nitro, tetrazolyl, thiazolyl, furanyl, pyridyl, trifluoromethyl, difluoromethyl, cyano, carboxyl, straight-chain or branched alkyl, alkoxy, alkoxycarbonyl or acyl each having up to 5 carbon atoms, or phenyl is optionally substituted by phenyl, which is optionally monosubstituted to disubstituted by chlorine, and salts thereof.

A process for the preparation of the compounds of the general formula (I) has additionally been found, characterized in that compounds of the general formula (II)

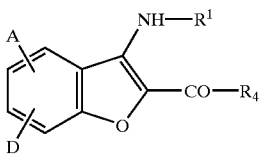

in which

A, D, $R^1$ and $R^4$ have the abovementioned meaning are reacted with compounds of the general formula (III)

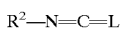

in which

L and $R^2$ have the abovementioned meaning, in inert solvents, if appropriate in the presence of a base and/or in the presence of an auxiliary, and in the case of $R^2/R^3$=H and L=O, compounds of the general formula (II) are reacted with compounds of the general formula (IIIa)

$$E\text{—}SO_2\text{—}N\text{=}C\text{=}O \quad (IIIa)$$

in which

E denotes halogen, preferably chlorine, and in the case of $R^2/R^3$=H and L=S, compounds of the general formula (II) are reacted with $NH_4SCN$, and in case of $R^1$, $R^2$ and/or $R^3 \neq H$ the amino groups are derivated optionally by common methods.

The process according to the invention can be illustrated by way of example by the following equations:

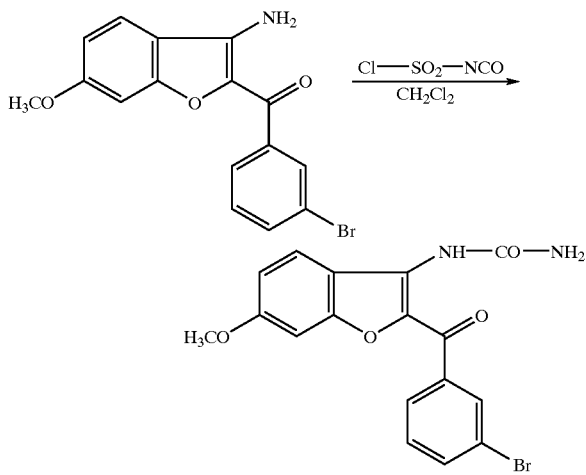

Suitable solvents are generally customary organic solvents which do not change under the reaction conditions. These include ethers such as diethyl ether, dioxane or tetrahydrofurane, acetone, dimethylsulfoxide, dimethylformamide or alcohols such as methanol, ethanol, propanol or halogenohydrocarbons such as dichlormethane, trichloromethane or tetrachloromethane. Dichloromethane is preferred.

Suitable bases are generally inorganic or organic bases. These preferably include alkali metal hydroxides such as, for example, sodium hydroxide, sodium hydrogencarbonate or potassium hydroxide, alkaline earth metal hydroxides such as, for example, barium hydroxide, alkali metal carbonates such as sodium carbonate, potassium carbonate, alkaline earth metal carbonates such as calcium carbonate, or alkaline metal or organic amines (trialkyl($C_1$–$C_6$)amines) such as triethylamine, or heterocycles such as 1,4-diazabicyclo[2.2.2]octane (DABCO), 1,8-diazabicyclo-[5.4.0]undec-7-ene (DBU), or amides such as sodium amides, lithium butyl amide or butyllithium, pyridine or methylpiperidine. It is also possible to employ alkali metals, such as sodium or its hydrides such as sodium hydride, as bases. Potassium carbonate, triethylamine, sodium hydrogencarbonate and sodium-hydroxide are preferred.

The process is in general carried out in a temperature range from −30° C. to +100° C., preferably from −10° C. to +50° C.

The process is generally carried out at normal pressure. However, it is also possible to carry out it at elevated pressure or at reduced pressure (for example in a range from 0.5 to 5 bar).

The base is employed in an amount from 1 mol to 10 mol, preferably from 1.0 mol to 4 mol, relative to 1 mol of the compounds of the general formulae (III) or (IIIa).

The compounds of the general formula (II) are as species new and are prepared by at first reacting compounds of the general formula (IV)

in which

A and D have the abovementioned meaning with compounds of the general formula (V)

$$R^4\text{—}CO\text{—}CH_2\text{—}T \quad (V)$$

in which $R^4$ has the abovementioned meaning and

T represents a typical leaving group such as, for example, chlorine, bromine, iodine, tosylate or mesylate, preferably bromine, to prepare compounds of the general formula (VI)

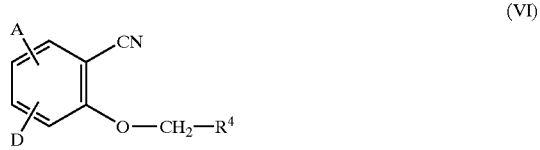

in which

A, D and $R^4$ have the abovementioned meaning, in one of the abovementioned solvents and bases, preferably triethylamine and di-methylformamide, which in a further last step are reacted with $NaOC_2H_5$/$C_2H_5OH$.

The process is in general carried out in a temperature range from +10° C. to +150° C., preferably from +30° C. to +80° C.

The process is generally carried out at normal pressure. However, it is also possible to carry out it at elevated pressure or at reduced pressure (for example in a range from 0.5 to 5 bar).

The compounds of the general formulae (III), (IIIa), (IV), (V) and (VI) are known and in some cases new and can be prepared by customary methods.

Surprisingly it was found that compounds given by the general formula (I) inhibited oxygen radical formation as well as TNFα (tumor necrosis factor) production, but potentiated the release of IL-10. These compounds elevated cellular cyclic AMP probably by inhibition of phagocyte phosphodiesterase activity.

The compounds according to the invention specifically inhibit the production of superoxide by polymorphonuclear leukocytes (PMN). Furthermore, these compounds inhibit TNFα release and potentiate IL-10 production in human monocytes in response to a variety of stimuli including bacterial lipopolysaccharide (LPS), complement-opsonized zymosan (ZymC3b) and IL-1β.

The described effects are probably mediated by the elevation of cellular cAMP probably due to inhibition of the type IV phosphodiesterase responsible for its degradation.

They can therefore be employed in medicaments for the treatment of acute and chronic inflammatory processes.

The compounds according to the invention are preferably suitable for the treatment and prevention of acute and chronic inflammation and auto immune diseases, such as emphysema, alveolitis, shock lung, all kinds of asthma, COPD, ARDS, bronchitis, arteriosclerosis, arthrosis, inflammations of the gastro-intestinal tract, rheumatoide arthritis myocarditis, sepsis and septic shock, arthritis, rheumatoid spondylitis and osteoarthritis, gram negative sepsis, toxic shock syndrome, acute respiratory distress syndrome, bone resorption diseases, reperfusion injury, graft vs host reaction, allograft rejection malaria, myalgias, HIV, AIDS, cachexia, Cronh's disease, ulcerative colitis, pyresis, system lupus erythematosus, multiple sclerosis, type I diabetes mellitus, psoriasis, Bechet's disease, anaphylactoid purpura nephritis, chronic glomerulonephritis, inflammatory bowel disease and leukemia. The compounds according to the invention are additionally suitable for reducing the damage to infarct tissue after reoxygenation. In this case the simultaneous administration of allopurinol to inhibit xanthine oxidase is of advantage. Combination therapy with superoxide dismutase is also of use.

Test Description

1. Preparation of Human PMN

Blood was taken from healthy subjects by venous puncture and neutrophils were purified by dextran sedimentation and resuspended in the buffered medium.

2. Inhibition of FMLP-stimulated Production of Superoxide Racidal Anions

Neutrophils ($2.5 \times 10^5$ ml$^{-1}$) were mixed with cytochrome C (1.2 mg/ml) in the wells of a microtitre plate. Compounds according to the invention were added in dimethyl sulphoxide (DMSO). Compound concentration ranged from 2.5 nM to 10 µM, the DMSO concentration was 0.1% v/v in all wells. After addition of cytochalasin b (5 µg×ml$^{-1}$) the plate was incubated for 5 min at 37° C. Neutrophils were then stimulated by addition of $4 \times 10^{-8}$ M FMLP and superoxide generation measured as superoxide dismutase inhibitable reduction of cytochrome C by monitoring the OD$_{550}$ in a Thermomax microtitre plate spectrophotometer. Initial rates were calculated using a Softmax kinetic calculation programme. Blank wells contained 200 units of superoxide dismutase.

The inhibition of superoxide production was calculated as follows:

$$\frac{[1-((Rx-Rb))]}{((Ro-Rb))} - 100$$

Rx=Rate of the well containing the compound according to the invention.
Ro=Rate in the control well.
Rb=Rate in the superoxide dismutase containing blank well.

Compounds according to the invention have IC$_{50}$ values in the range 0.07 µM-10 µM.

3. Measurement of PMN Cyclic AMP Concentration

The compounds according to the invention were incubated with $3.7 \times 10^6$ PMN for 5 min at 37° C. before addition of $4 \times 10^{-8}$ M FMLP. After 6 min protein was precipitated by the addition of 1% v/v conc. HCl in 96% v/v ethanol containing 0.1 mM EDTA. After centrifugation the ethanolic extracts were evaporated to dryness under N$_2$ and resuspended in 50 mM Tris/HCl pH 7.4 containing 4 mM EDTA. The cyclic AMP concentration in the extracts was determined using a cyclic AMP binding protein assay supplied by Amersham International plc. Cyclic AMP concentrations were expressed as percentage of vehicle containing control incubations.

Compounds elavate the cAMP-level at 1 µM compound 0-400% of control values.

4. Assay of PMN Phosphodiesterase

This was performed as a particulate fraction from human PMN essentially as described by Souness and Scott (Biochem. J. 291, 389–395, 1993). Particulate fractions were treated with sodium vanadate/glutathione as described by the authors to express the descrete stereospecific site on the phosphodiesterase enzyme. Compounds according to the invention had IC$_{50}$ values ranging from 0.001 µM to 10 µM.

5. Assay of Human Platelet Phosphodiesterase

This was performed essentially as described by Schmidt et al (Biochem. Pharmacol. 42, 153–162, 1991) except that the homogenate was treated with vanadate glutathione as above. Compounds according to the invention had IC$_{50}$ values greater than 100 µM.

6. Assay of Binding to the Rolipram Binding Site in Rat Brain Membranes

This was performed essentially as described by Schneider et al. (Eur. J. Pharmacol. 127, 105–115, 1986). Compounds according to the invention had IC$_{50}$ values in the range 0.01 to 10 µM.

7. Preparation of Human Monocytes

Blood was taken from normal donors. Monocytes were isolated from peripheral blood by density centrifugation, followed by centrifugal elutriation.

8. Endotoxin Induced TNF Release

Monocytes ($1 \times 10^6$ ml$^{-1}$) were stimulated with LPS (2 µg ml$^{-1}$) and coincubated with the compounds at different concentrations ($10^{-4}$ to 10 µg ml$^{-1}$). Compounds were dissolved in DMSO/medium (2% v/v). The cells were incubated in RPMI-1640 medium glutamine/FCS supplemented and at 37° C. in a humidified atmosphere with 5% CO$_2$. After 18 to 24 hours TNF was determined in the supernatants by an human TNF specific ELISA (medgenix). Controls were nonstimulated and LPS stimulated monocytes without compounds.

Example 2, 13 and 16 induce inhibition of LPS driven TNF activity in human monocytes (IC$_{50}$: $10^{-3}$ to 1 µg ml$^{-1}$).

9. Endotoxin Induced Shock Lethality in Mice

B6D2F1 mice (n=10) were sensitized with galactosamine (600 mg/kg), and shock and lethality were triggered by LPS (0.01 µg/mouse). The compounds were administered intravenously 1 hour prior LPS. Controls were LPS challenged mice without compound. Mice were dying 8 to 24 hours post LPS challenge. Example 2, 13 and 16 reduced the endotoxin medicated mortality about 70% to 100% at doses of 3 to 30 mg/kg.

The galactosamine/LPS mediated mortality was reduced.

10. Stimulation of Human Monocytes and Determination of Cytokine Levels

Human monocytes ($2 \times 10^5$ in 1 ml) were stimulated with 100 ng/ml LPS, 0.8 mg/ml zymC3b or 10 ng/ml IL-1β in the presence of test compounds. The final DMSO concentration was maintained at 0.1% v/v. Cells were incubated overnight in a humidified atmosphere of 5% CO$_2$ at 37° C. Supernatants were harvested and stored at −70° C. The TNFα concentration was measured by ELISA using the A6 anti-TNF monoclonal antibody (Miles) as the primary antibody. The secondary antibody was the polyclonal anti-TNFα antibody IP300 (Genzyme) and the detection antibody was a polyclonal anti-rabbit IgG alkaline phosphatase conjugate (Sigma). IL-10 was determined by ELISA (Biosource). Example 2 inhibits the LPS- and IL-1β-induced TNFα production with an IC$_{50}$ of 1–2 µM, while the zymC3b-induced TNFα production was inhibited by approximately 50% at 10 µM. Example 2 also potentiates the release of IL-10, without stimulating IL-10 production by itself. There is approximately a 3–4 fold increase in IL-10 production at 10 µM.

The new active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can be used as auxiliary solvents if appropriate.

Administration is carried out in a customary manner, preferably orally or parenterally, in particular perlingually or intravenously.

In the case of parenteral administration, solutions of the active compound can be employed using suitable liquid vehicles.

In general, it has proved advantageous on intravenous administration to administer amounts from about 0.001 to 10 mg/kg, preferably about 0.01 to 5 mg/kg of body weight to achieve effective results, and on oral administration the dosage is about 0.01 to 25 mg/kg, preferably 0.1 to 10 mg/kg of body weight.

In spite of this, it may be necessary to depart from the amounts mentioned, in particular depending on the body weight or the type of application route, on individual behaviour towards the medicament, the manner of its formulation and the time or interval at which administration takes place. Thus, in some cases it may be sufficient to manage with less than the abovementioned minimum amount, while in other cases the upper limit mentioned must be exceeded. In the case of administration of relatively large amounts, it is advisable to divide these into several individual doses over the course of the day.

Solvent

I petrolether: ethylacetate 1:1
II petrolether: ethylacetate 5:1
III petrolether: ethylacetate 5:2
IV ethylacetate
V dichlormethane:methanol 5:1
VI dichlormethane
VII cyclohexane:ethylacetate 3:1
VIII dichlormethane:methanol 50:1

Starting Compounds

Example I

2-Hydroxy-4-methoxybenzonitrile

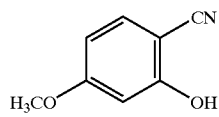

2-Hydroxy-4-methoxybenzaldehyde (55 g; 0.36 mol), hydroxylamine hydrochloride (30 g; 0.43 mol) and sodium formate (34 g; 0.5 mol) were refluxed in formic acid (200 ml; 98–100%) for 1.25 h. The solution was then rapidly chilled in an ice bath, with stirring over 30 min. The resulting precipitate was separated by filtration and washed well with water. Following drying, in a desicator under vacuum, the title compound was obtained (45 g; 0.3 mol; 84% yield) as a brick-red solid, mp 169–171° C., rf (EtOAc) 0.43.

Example II (3-Amino-6-methoxy-benzofuran-2-yl)-(3-nitro-phenyl)-methanone

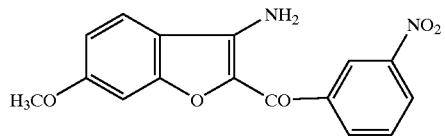

Equivalent amounts, 5 g (33.5 mmol) of 2-Hydroxy-4-methoxy-benzonitrile and 8.2 g (33.5 mol) of ω-Bromo-3-nitroacetophenone were dissolved in 30 ml DMF and 4.6 ml triethylamine were added. The mixture was heated to 75° C. for 90 min, quenched with water and extracted 3 times with dichloromethane. The solvent was distilled of in vacuo and the residue dried over night. The crude product was heated under reflux in a mixture of 150 mg sodium in 50 ml ethanol for 90 min. After cooling to room temperature the solvent was distilled of, the residue solved in water and extracted 3 times with ethylacetate. The organic layer was dried over Na$_2$SO$_4$, concentrated in vacuo and the residue was further purified by chromatography (silica gel 60).

Yield: 9.6 g (92%)

R$_f$: 0.18 (III)

Melting point: 214° C.

The compounds shown in tables I–V are prepared in analogy to the procedure of example I.

TABLE I

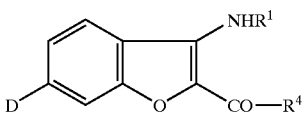

| Ex.-No. | D | R¹ | R⁴ | Mp. (° C.) | Yield (% of theory) | $R_f$* |
|---|---|---|---|---|---|---|
| III | —OCH₃ | —CO—CH₃ | 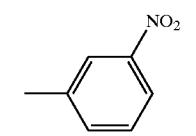 3-NO₂-phenyl | 202 | 100 | 0.39 (V) |
| IV | —OCH₃ | H | 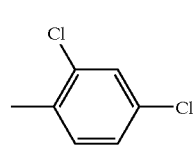 2,4-diCl-phenyl | 162 | 57 | 0.73 (V) |
| V | —OCH₃ | —CO—CO₂CH₃ | 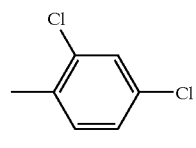 2,4-diCl-phenyl | 190 | 34 | 0.43 (VI) |
| VI | —OCH₃ | —CO₂CH₃ | 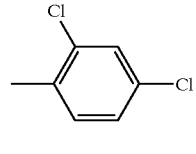 2,4-diCl-phenyl | 107 | 9 | 63 (VI) |
| VII | —OCH₃ | —CO—CO₂H | 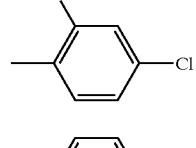 2,4-diCl-phenyl | 166 | 32 | 0.09 (V) |
| VIII | —OCH₃ | —CH₃ | 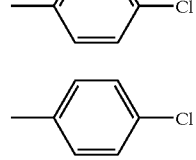 2,4-diCl-phenyl | 119–121 | 30 | 0.62 (IV) |
| IX | —OCH₃ | —CO—CO₂C₂H₅ | 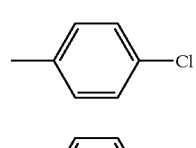 4-Cl-phenyl | 159 | 70 | 0.53 (VI) |
| X | —OCH₃ | —CO—CO₂H | 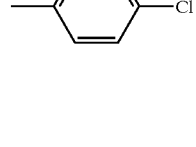 4-Cl-phenyl | 199 | 87 | 0.07 (V) |
| XI | —OCH₃ | H |  4-Cl-phenyl | 183 | 99 | 0.69 (V) |
| XII | —OCH₃ | —CO—CH₃ | 4-Cl-phenyl | 179 | 70 | 0.87 (V) |

TABLE I-continued
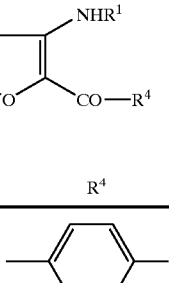
| ExNo. | D | R¹ | R⁴ | Mp. (° C.) | Yield (% of theory) | R_f* |
|---|---|---|---|---|---|---|
| XIII | —OCH₃ | —CO—(CH₂)₂—CH₃ |  | 131.5 | 60 | 0.57 (V) |
| XIV | —OCH₃ | 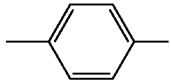 | 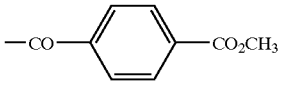 | 124.5 | 54 | 0.62 (VI) |
| XV | —OCH₃ | 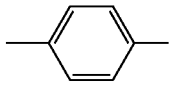 | 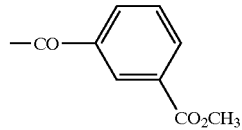 | 238 | 41 | 0.43 (VI) |
| XVI | —OCH₃ | 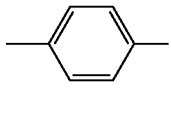 |  | 202 | 50 | 0.41 (VI) |
| XVII | —OCH₃ | 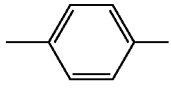 | 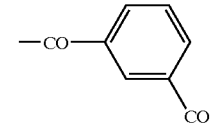 | 308 | 11 | 0.32 (V) |
| XVIII | —OCH₃ | 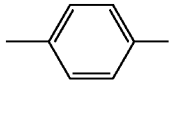 | 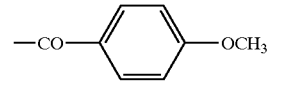 | 279 | 45 | 0.37 (V) |
| XIX | —OCH₃ | 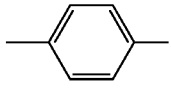 | 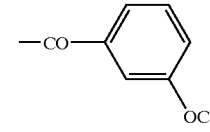 | 206 | 72 | 0.59 (VI) |
| XX | —OCH₃ | 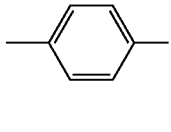 | 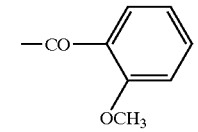 | 177 | 80 | 0.58 (VI) |
| XXI | —OCH₃ | 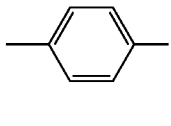 | 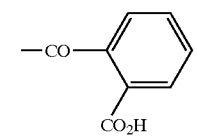 | 155 (dec) | 74 | 0.1 (VI) |
| XXII | —OCH₃ | 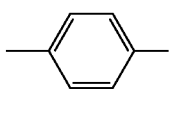 | 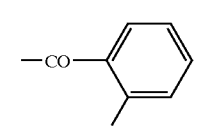 | 163 | 72 | 0.44 (VI) |
| XXIII | —OCH₃ | 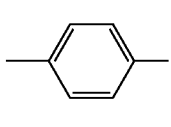 | | 139 | 44 | 0.44 (V) |

TABLE I-continued
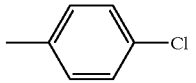
| Ex.-No. | D | R¹ | R⁴ | Mp. (° C.) | Yield (% of theory) | R_f* |
|---|---|---|---|---|---|---|
| XXIV | —OCH₃ | —CO—(CH₂)₃—Br | 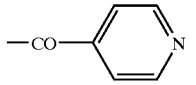 4-Cl-C₆H₄ | 177 | 84 | 0.64 (VI) |
| XXV | —OCH₃ | —CO-pyridin-4-yl | 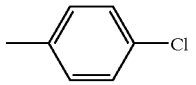 4-Cl-C₆H₄ | 230 | 64 | 0.77 (V) |
| XXVI | —OCH₃ | H | 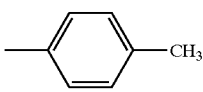 4-CH₃-C₆H₄ | 238 | 91 | 0.66 (IV) |
| XXVII | —OCH₃ | —CO—CH₂—CO₂C₂H₅ | 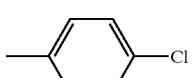 4-Cl-C₆H₄ | 129 | 16 | 0.92 (V) |
| XXVIII | —OCH₃ | H | 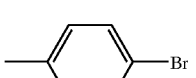 4-Br-C₆H₄ | 122 | 82 | 0.62 (IV) |
| XXIX | —OCH₃ | H | 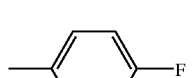 4-F-C₆H₄ | 149–151 | 56 | 0.64 (IV) |
| XXX | —OCH₃ | H |  3-Br-C₆H₄ | 135 | 30 | 0.6 (I) |
| XXXI | —OCH₃ | H | 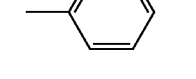 3-OCH₃-C₆H₄ | 123 | 89 | 0.7 (I) |
| XXXII | —OCH₃ | H | 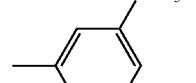 2-CF₃-C₆H₄ | 136 | 41 | 0.8 (I) |
| XXXIII | —OCH₃ | H | 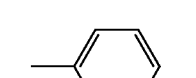 2-F-C₆H₄ | 137 | 47 | 0.3 (III) |
| XXXIV | —OH | H | 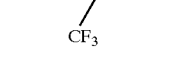 2,4-Cl₂-C₆H₃ | | 19 | 0.56 (IV) |

TABLE I-continued

[Structure: benzofuran with D at 6-position, NHR¹ at 3-position, CO—R⁴ at 2-position]

| Ex.-No. | D | R¹ | R⁴ | Mp. (° C.) | Yield (% of theory) | R_f* |
|---|---|---|---|---|---|---|
| XXXV | —OCH₃ | H | 2,4,6-trimethylphenyl (H₃C, H₃C, CH₃) | 214 | 90 | 0.67 (IV) |

TABLE II

[Structure: benzofuran with D at 5-position, NHR¹ at 3-position, CO-R⁴ at 2-position]

| Ex.-No. | D | R¹ | R⁴ | Mp. (° C.) | Yield (% of theory) | R_f* |
|---|---|---|---|---|---|---|
| XXXVI | OCH₃ | H | 2,4-dichlorophenyl | 90 | 90 | 0.1 (VI) |
| XXXVII | OCH₃ | H | 4-fluorophenyl | 155 | 62 | 0.4 (VI) |
| XXXVIII | OCH₃ | H | 4-methylphenyl | 170 | quant. | 0.6 (VI) |
| XXXIX | OCH₃ | H | 4-ethylphenyl (C₂H₅) | 220 | 9 | 0.65 (VI) |
| XL | OCH₃ | H | 4-chlorophenyl | 258 | 63 | 0.33 (I) |
| XLI | OCH₃ | H | 3-chlorophenyl | 130 | 61 | 0.4 (I) |

TABLE III
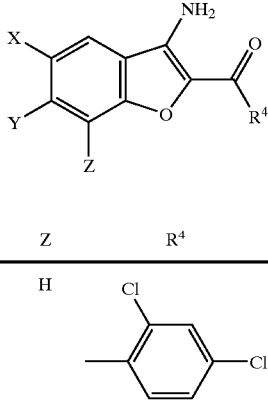
| Ex.-No. | X | Y | Z | R⁴ | Mp. (° C.) | Yield (% of theory) | R_f |
|---|---|---|---|---|---|---|---|
| XLII | H | COCH₃ | H | 2,4-dichlorophenyl | 209 | 19 | 0.72 (V) |
| XLIII | H | COCH₃ | H | 3-bromophenyl | 198 | 37 | 0.7 (V) |
| XLIV | H | NHSO₂-phenyl | H | 2,4-dichlorophenyl | 223 | 25 | 0.71 (V) |
| XLV | H | COOCH₃ | H | 3-bromophenyl | 253 | 30 | 0.72 (V) |
| XLVI | H | COOCH₃ | H | 2,4-dichlorophenyl | 258 | 51 | 0.70 (V) |
| XLVII | H | NHSO₂-phenyl | H | 3-bromophenyl | 210 | 72 | 0.67 (V) |
| XLVIII | H | CF₃ | H | 2,4-dichlorophenyl | | | |
| XLIX | H | CN | H | 2,4-dichlorophenyl | | | |
| L | H | NO₂ | H | 2,4-dichlorophenyl | | | |

TABLE III-continued
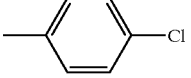
| Ex.-No. | X | Y | Z | R⁴ | Mp. (° C.) | Yield (% of theory) | R_f |
|---|---|---|---|---|---|---|---|
| LI | H | CH₃ | H | 2,4-dichlorophenyl | | | |
| LII | H | OCH₃ | H | 2,4-dichlorophenyl | | | |
TABLE IV
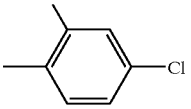
| Ex.-No. | X | Y | Z | R⁴ | Mp. (° C.) | Yield (% of theory) | R_f |
|---|---|---|---|---|---|---|---|
| LIII | H | H | OCH₃ | 2,4-dichlorophenyl | 210 | 57 | 0.4 (III) |
| LIV | H | H | OCH₃ | 3-bromophenyl | 157 | 41 | 0.44 (III) |
| LV | OCH₃ | H | H | 2,4-dimethylphenyl | 147 | 69 | 0.78 (V) |
| LVI | Cl | OCH₃ | H | 2,4-dichlorophenyl | 214 | 62 | 0.4 (V) |
| LVII | H | —OCH₂-phenyl | H | 2,4-dichlorophenyl | 150 | 46 | 0.5 (V) |

TABLE IV-continued
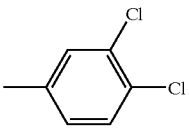
| Ex.-No. | X | Y | Z | R⁴ | Mp. (° C.) | Yield (% of theory) | R_f |
|---|---|---|---|---|---|---|---|
| LVIII | OCH₃ | H | H | 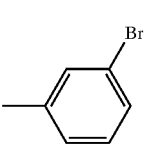 | 178 | 68 | 0.7 (V) |
| LIX | OCH₃ | H | H | 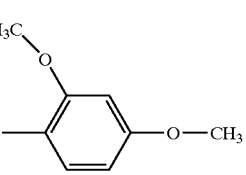 | 125 | 39 | 0.78 (V) |
| LX | OCH₃ | H | H | 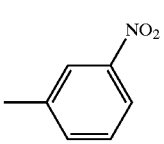 | 127 | 59.4 | 0.65 (V) |
| LXI | OCH₃ | H | H | 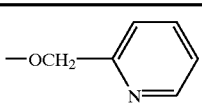 | 171 | 47 | 0.83 (V) |
TABLE V
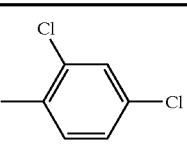
| Ex.-No. | X | Y | Z | R | Mp. (° C.) | Yield (% of theory) | R_f |
|---|---|---|---|---|---|---|---|
| LXII | H | —OCH₂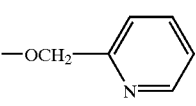 | H | 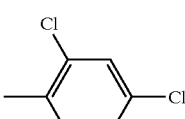 | | | |
| LXIII | —OCH₂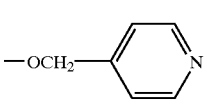 | H | H | 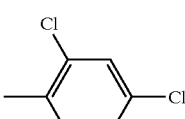 | | | |
| LXIV | —OCH₂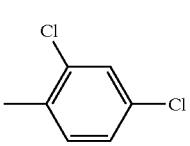 | H | H | 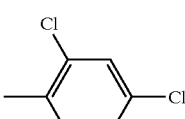 | | | |

TABLE V-continued

| Ex.-No. | X | Y | Z | R | Mp. (° C.) | Yield (% of theory) | $R_f$ |
|---|---|---|---|---|---|---|---|
| LXV | H | OCF$_3$ | H |  | | | |
| LXVI | H | NH$_2$ | H | 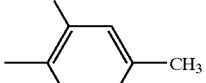 | | | |
| LXVII | H | OCH$_3$ | H | 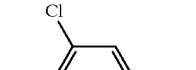 | 155 | 18 | 0.5 (III) |
| LXVIII | H | CONH$_2$ | H |  | | | |
| LXIX | H | OC$_2$H$_4$OH | H | 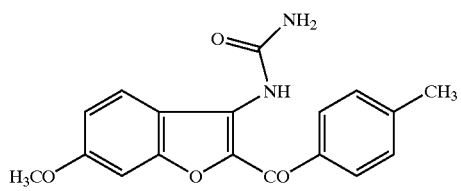 | | | |

PREPARATION EXAMPLES

Example 1

N-(3-(6-methoxy-2-(4'-methylbenzoyl)benzofuranyl) urea

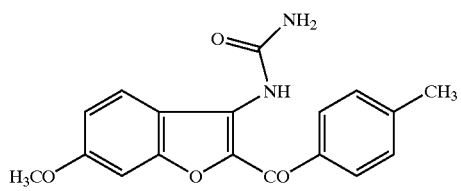

1 g (3.55 mmol) compound of example II was dissolved in dichloromethane (20 ml), cooled to 0° C. and chlorosulphonylisocyanate (0.55 g, 3.99 mmol) in dichloromethane (10 ml) was added dropwise over 30 min., after which the reaction was brought to room temperature and stirred for an additional 4 h. Water (20 ml) was added and the reaction stirred overnight. The dichloromethane was removed under vacuum and the residue taken up in ethylacetate, washed with brine, separated and dried over MgSO$_4$. Evaporation affored a solid which was triturated with pentane to give the title compound (1 g; 3.1 mmol; 87%) as a yellow solid, mp 258–260° C., rf (CH$_3$OH: CH$_2$Cl$_2$ 1:1)0.82.

The compounds shown in table 1 were prepared in analogy to the procedure of example 1:

TABLE 1
| Ex.-No. | D | L | R² | R³ | R⁴ | Yield (% of theory) | Mp. (° C.) | R_f* |
|---|---|---|---|---|---|---|---|---|
| 2 | —OCH₃ | O | H | H | 2,4-dichlorophenyl | 82 | 218 (dec) | 0.2 (V) |
| 3 | —OCH₃ | O | H | H | 4-bromophenyl | 92 | 264 | 0.54 (V) |
| 4 | —OCH₃ | O | H | H | 4-chlorophenyl | 87 | 266 | 0.55 (V) |
| 5 | —OCH₃ | O | H | H | 4-fluorophenyl | 14 | 206–7 | 0.65 (V) |
| 6 | —OCH₃ | O | H | H | 3-nitrophenyl | 59 | 23 | 0.2 (V) |
| 7 | H₃CO₂C—O | O | H | H | 2,4-dichlorophenyl | 53 | 208–9 | 0.6 (V) |
| 8 | HO | O | H | H | 2,4-dichlorophenyl | 65 | 337–9 | 0.12 (V) |
| 9 | H₃C—O | O | H | —CH₃ | 2,4-dichlorophenyl | 56 | 174 | 0.87 (V) |
| 10 | H₃C—O | O | —CH₃ | —CH₃ | 2,4-dichlorophenyl | 22 | 204 | 0.7 (V) |
| 11 | H₃C—O | O | H | H | 2,4,6-trimethylphenyl | 41 | 217 | 0.62 (IV) |

TABLE 1-continued

[Structure: benzofuran with D substituent, NH-C(=L)-NR²R³ at position 3, CO-R⁴ at position 2]

| Ex.-No. | D | L | R² | R³ | R⁴ | Yield (% of theory) | Mp. (° C.) | $R_f$* |
|---|---|---|---|---|---|---|---|---|
| 12 | H₃C—O | O | H | H | 3-bromophenyl | 89 | 200 | 0.5 (I) |
| 13 | H₃C—O | O | H | H | 3-methoxyphenyl | 91 | 201 | 0.4 (I) |
| 14 | H₃C—O | O | H | H | 2-(trifluoromethyl)phenyl | 93 | 212 | 0.2 (III) |
| 15 | H₃C—O | O | H | H | 2-fluorophenyl | 67 | 204 | 0.2 (III) |
| 16 | H₃C—O | O | H | H | 3-chlorophenyl | 63 | 187 | 0.7 (V) |
| 17 | H₃C—O | O | H | —CH₂—CH=CH₂ | 2-fluorophenyl | 54 | 174 | 0.9 (V) |
| 18 | H₃C—O | O | H | cyclohexyl | 3-bromophenyl | 100 | 142 | 0.49 (II) |
| 19 | H₃C—O | O | H | —CH₂—CH=CH₂ | 2-(trifluoromethyl)phenyl | 16 | 207 | 0.21 (II) |

TABLE 1-continued

| Ex.-No. | D | L | R² | R³ | R⁴ | Yield (% of theory) | Mp. (° C.) | R$_f$* |
|---|---|---|---|---|---|---|---|---|
| 20 | H₃C—O | O | 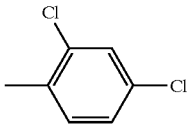 | | 2,4-dichlorophenyl | 18 | 187 | 0.89 (V) |

Example 21

N-benzoyl-N-'(3-(2-(2',4'-dichlorobenzoyl)-6-methoxybenzofuranyl)thiourea

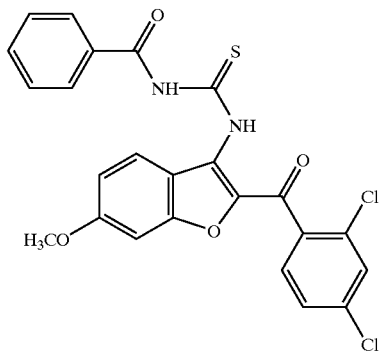

1.35 g (4 mmol) of the compound from example IV and benzoylisothiocyanate (720 mg; 4.4 mmol) were refluxed in acetone (20 ml) for 24 h, after which time the reaction was cooled and poured onto iced water with stirring. The precipitate was isolated by filtration and washed with water. After drying, in a desicator under vacuum, the title compound was isolated (1.6 g; 3.3 mmol; 84% yield) as a yellow solid, mp 100–102° C., rf 0.67 (IV).

The compounds shown in table 2–6 were prepared in analogy to the procedure of example 1:

TABLE 2

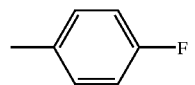

| Ex.-No. | D | L | R² | R³ | R⁴ | Yield (% of theory) | Mp. (° C.) | R$_f$* |
|---|---|---|---|---|---|---|---|---|
| 22 | OCH₃ | O | H | H | 4-fluorophenyl | 49 | 228 (dec) | 0.34 (I) |
| 23 | OCH₃ | O | H | H | 2,4-dichlorophenyl | 29.5 | 231 (dec.) | 0.42 (I) |
| 24 | OCH₃ | O | H | H | 4-chlorophenyl | 63 | 258 | 0.33 (I) |

TABLE 2-continued

[Structure: 5-D-benzofuran with 3-NH-C(=L)-NR²R³ and 2-CO-R⁴]

| Ex.-No. | D | L | R² | R³ | R⁴ | Yield (% of theory) | Mp. (° C.) | R_f* |
|---|---|---|---|---|---|---|---|---|
| 25 | OCH₃ | O | H | H | | 50.4 | 222 | 0.33 (I) |
| 26 | OCH₃ | O | H | H | | 9 | 217 | 0.36 (I) |
| 27 | OCH₃ | O | H | H | | 33.5 | 214 | 0.4 (I) |

TABLE 3

[Structure: benzofuran with X, Y, Z substituents, 3-NH-C(=O)-NH₂ urea, and 2-C(=O)-R⁴]

| Ex.-No. | X | Y | Z | R⁴ | Mp. (° C.) | Yield (% of theory) | R_f |
|---|---|---|---|---|---|---|---|
| 28 | H | H | OCH₃ | 2,4-dichlorophenyl | 250 (Z) | 46 | 0.7 (V) |
| 29 | H | H | OCH₃ | 3-bromophenyl | 226 (Z) | 98 | 0.04 (III) |
| 30 | OCH₃ | H | H | 2,4-dimethylphenyl | 266 | 64 | 0.54 (V) |
| 31 | Cl | OCH₃ | H | 2,4-dichlorophenyl | — | 89 | 0.6 (V) |
| 32 | H | OCH₂-phenyl | H | 2,4-dichlorophenyl | 193 | 96 | 0.83 (V) |

TABLE 3-continued

| Ex.-No. | X | Y | Z | R⁴ | Mp. (° C.) | Yield (% of theory) | R_f |
|---|---|---|---|---|---|---|---|
| 33 | OCH₃ | H | H | 3,4-dichlorophenyl | 246 | 89 | 0.56 (V) |
| 34 | OCH₃ | H | H | 3-bromophenyl | 217 | 30 | 0.61 (V) |
| 35 | OCH₃ | H | H | 2,4-dimethoxyphenyl | 202 | 50 | 0.52 (V) |
| 36 | OCH₃ | H | H | 3-nitrophenyl | 234 | 79 | 0.41 (V) |

TABLE 4

| Ex.-No. | X | Y | Z | R⁴ | Mp. (° C.) | Yield (% of theory) | R_f |
|---|---|---|---|---|---|---|---|
| 37 | H | COCH₃ | H | 2,4-dichlorophenyl | 195 | 35 | 0.3 (III) |
| 38 | H | COCH₃ | H | 3-bromophenyl | — | 27 | 0.34 (III) |

TABLE 4-continued

[Structure: benzofuran with X, Y, Z substituents on benzene ring; position 3 has NH-C(=O)-NH₂ (urea); position 2 has C(=O)-R⁴]

| Ex.-No. | X | Y | Z | R⁴ | Mp. (° C.) | Yield (% of theory) | $R_f$ |
|---|---|---|---|---|---|---|---|
| 39 | H | NHSO₂-phenyl | H | 2,4-dichlorophenyl | | 17 | 0.54 (III) |
| 40 | H | COOCH₃ | H | 3-bromophenyl | 146 | 35 | 0.88 (V) |
| 41 | H | COOCH₃ | H | 2,4-dichlorophenyl | 245 | 37 | 0.77 (V) |
| 42 | H | NHSO₂-phenyl | H | 3-bromophenyl | 221 | 20 | 0.44 (V) |
| 43 | H | CF₃ | H | 2,4-dichlorophenyl | | | |
| 44 | H | CN | H | 2,4-dichlorophenyl | | | |
| 45 | H | NO₂ | H | 2,4-dichlorophenyl | | | |

TABLE 5

[Structure: 5,6-disubstituted benzofuran with 3-position bearing NH-C(=S)-NH-R³ thiourea group and 2-position bearing C(=O)-R⁴]

| Ex.-No. | R³ | R⁴ | X | Y | Yield (% of theory) | R_f |
|---|---|---|---|---|---|---|
| 46 | COOC₂H₅ | 2,4-dichlorophenyl | OCH₃ | H | 62 | 0.34 (V) |
| 47 | COOC₂H₅ | 2,4-dichlorophenyl | H | OCH₃ | 56 | 0.38 (VII) |

TABLE 6

[Structure: 5,6,7-trisubstituted benzofuran with 3-position bearing NH-C(=O)-NH₂ urea group and 2-position bearing C(=O)-R⁴]

| Ex.-No. | X | Y | Z | R⁴ | Mp. (° C.) | Yield (% of theory) | R_f |
|---|---|---|---|---|---|---|---|
| 48 | H | OCH₂-(2-pyridyl) | H | 2,4-dichlorophenyl | | | |
| 49 | OCH₂-(2-pyridyl) | H | H | 2,4-dichlorophenyl | | | |
| 50 | OCH₂-(4-pyridyl) | H | H | 2,4-dichlorophenyl | | | |
| 51 | H | CH₃ | H | 2,4-dichlorophenyl | 224 | 31 | 0.5 (V) |

TABLE 6-continued
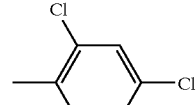
| Ex.-No. | X | Y | Z | R⁴ | Mp. (° C.) | Yield (% of theory) | R_f |
|---|---|---|---|---|---|---|---|
| 52 | H | OCF₃ | H | 2,4-dichlorophenyl | | | |
| 53 | H | NH₂ | H | 2,4-dichlorophenyl | | | |
| 54 | H | OCH₃ | H | 2,4-dimethylphenyl | 217 | 70 | 0.27 (III) |
| 55 | H | CONH₂ | H | 2,4-dichlorophenyl | | | |
| 56 | H | OC₂H₄OH | H | 2,4-dichlorophenyl | | | |
| 57 | H | OCH₂CO₂CH₃ | H | 2,4-dichlorophenyl | | | |
| 58 | H | OSO₂CH₃ | H | 2,4-dichlorophenyl | | | |
| 59 | H | OCH(CH₃)₂ | H | 2,4-dichlorophenyl | | | |
| 60 | H | OC₂H₅ | H | 2,4-dichlorophenyl | | | |

TABLE 6-continued

| Ex.-No. | X | Y | Z | R⁴ | Mp. (° C.) | Yield (% of theory) | $R_f$ |
|---|---|---|---|---|---|---|---|
| 61 | H | NHCCH₃ (O) | H | 2,4-dichlorophenyl | | | |

What is claimed is:

1. A N-(3-benzofuranyl)urea-derivative of a formula (I)

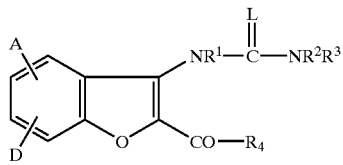

in which

A and D are identical or different and represent hydrogen, straight chain or branched acyl or alkoxycarbonyl, each having up to 6 carbon atoms, or straight chain or branched alkyl having up to 6 carbon atoms, which is optionally substituted by carboxyl or alkoxycarbonyl having up to 6 carbon atoms, phenoxy or benzoyl, or represent halogen, carboxyl, cyano, nitro, trifluoroinethyl, trifluoromethoxy or a group of a formula —$OR^5$, —$S(O)_aR^6$, —$(O—CH_2—CO)_b$—$NR^7R^8$, —$CO—NR^9R^{10}$, —$SO_2—NR^{11}R^{12}$ or —$NH—SO_2R^{13}$, in which $R^5$, $R^6$, $R^8$, $R^9$, $R^{10}$, $R^{10}$ and $R^{12}$ are identical or different and denote hydrogen, cycloalkyl having 3 to 6 carbon atoms, or benzyl and which is optionally substituted by identical or different substituents from the group consisting of halogen, cyano, nitro, and a straight chain or branched alkyl having up to 6 carbon atoms or denote straight chain or branched alkyl, alkenyl or acyl each having up to 8 carbon atoms, or denote phenyl, which is optionally monosubstituted to disubstituted by identical or different substituents from the group consisting of nitro, halogen, carboxy and straight chain or branched alkoxycarbonyl having up to 6 carbon atoms, or $R^5$ denotes a hydroxyl protecting group selected from the group consisting of benzyl and acetyl, or straight chain or branched alkoxycarbonyl having up to 6 carbon atoms, or denotes straight chain or branched alkyl having up to 8 carbon atoms, which is substituted by carboxyl, hydroxyl, straight chain or branched acyl or alkoxycarbonyl each having up to 6 carbon atoms, phenoxyl, or benzoyl which is optionally substituted by halogen, cyano, nitro or by straight chain or branched alkyl having up to 6 carbon atom;

or $R^5$ denotes a group of a formula $SO_2R^{14}$, in which $R^{14}$ denotes phenyl, trifluoromethyl or straight chain or branched alkyl having up to 4 carbon atoms, a denotes a number 0, 1 or 2, b denotes a number 0 or 1, $R^7$ denotes hydrogen or a straight chain or branched alkyl having up to 4 carbon atoms, $R^{13}$ denotes aryl having up 6 to 10 carbon atoms, trifluoromethyl or straight chain or branched alkyl having up to 6 carbon atoms, $R^1$ represents hydrogen, straight chain or branched alkyl having up to 6 carbon atoms, an aminoprotecting group selected from the group consisting of benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxvcarbonyl, 2-nitro-4,5-dimethoxyhenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, allyloxycarbonyl, vinyloxycarbonyl, 2-nitrobenzyloxycarbonyl, 3,4,5-trimethoxybenzyloxycarbonyl, cyclohexoxycarbonyl, 1,1-dimethylethoxycarbonyl, adamantylcarbonyl, phthaloyl, 2,2,2-trichlorethoxycarbonyl, 2,2,2-trichloro-tert-butoxycarbonyl, menthyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2-bromoacetyl, 2,2,2-trifluoroacetyl, 2,2,2-trichioracetyl, benzoyl, 4-chlorobenzoyl, 4-bromobenzoyl, 4-nitrobenzoyl, isovaleroyl, benzyloxymethylenyl, 4-nitrobenzyl, 2,4- dinitirobenzyl and 4-nitrophenyl, or a group of the formula —CO—R$^{15}$, in which R$_{15}$ denotes hydroxyl, straight chain or branched alkoxycarbonyl having up to 6 carbon atoms, cycloalkyl having up 3 to 6 carbon atoms, or straight chain or branched alkyl having up to 8 carbon atoms, which is optionally substituted by halogen, carboxyl or straight chain or branched alkoxycarbonyl having up to 6 carbon atoms, or denotes phenyl, which is optionally substituted by hydroxyl, carboxyl or straight chain or branched alkoxy or alkoxycarbonyl each having up to 6 carbon atoms, L represents an oxygen or sulfur atom, R$^2$ and R$^3$ are identical or different and represent hydrogen, cycloalkyl having up to 6 carbon atoms, straight chain or branched alkyl, alkoxycarbonyl or alkenyl each having up to 8 carbon atoms, or represent benzoyl or aryl having 6 to 10 carbon atoms, which are optionally monosubstituted to trisubstituted by identical or different substituents from the group consisting of halogen, cyano, nitro, carboxyl, and straight chain or branched alkyl, alkoxy, alkoxycarbonyl or acyl each having up to 6 carbon atoms, and R$^4$ represents phenyl, which is optionally monosubstituted to trisubstituted by identical or different substituents from the group consisting of hydroxyl, cycloalkyl having up to 3 to 6 carbon atoms, halogen, nitro, trifluoromethyl, difluoromethyl, cyano, carboxyl, and straight chain or branched alkyl, alkoxy, alkoxycarbonyl or acyl each having up to 8 carbon atoms, or phenyl is optionally substituted by phenyl, which is optionally monosubstituted to disubstituted by halogen, or by a group of a formula —NR$^{16}$R$^{17}$, —SR$^{18}$, SO$_2$R$^{19}$ or —O—SO$_2$R$^{20}$, in which R$^{16}$ and R$^{17}$ have the abovementioned meaning of R$^7$ and R$^5$ and are identical or different to the latter, or R$^{16}$ denotes hydrogen, and R$^{17}$ denotes straight chain or branched acyl having up to 6 carbon atoms, R$^{18}$ denotes hydrogen or straight chain or branched alkyl having up to 6 carbon atoms, R$^{19}$ and R$^{20}$ are identical or different and represent straight chain or branched alkyl having up to 6 carbon atoms, benzyl or phenyl, or a salt thereof.

2. The N-(3-benzofuranyl)urea-derivative of the formula according to claim 1, in which A and D are identical or different and represent hydrogen, straight chain and branched acyl or alkoxycarbonyl each having up to 5 carbon atoms or straight chain or branched alkyl having up to 4 carbon atoms which is optionally substituted by carboxyl, hydroxyl, alkoxycarbonyl having up to 5 carbon atoms, phenoxy or benzoyl, or represent fluorine, chlorine, bromine, nitro, trifluoromethyl or a group of a formula —OR$^5$, —S(O)$_a$—R$^6$, (O—CH$_2$—CO)$_b$-NR$^7$R$^8$, —CO—NR$^9$R$^{10}$, —SO—NR$^{11}$R$^{12}$ or —NH—SO$_2$—R$^{13}$, in which R$^5$, R$^6$, R$^8$, R$^9$, R$^{10}$, R$^{11}$ and R$^{12}$ are identical or different and denote hydrogen, cyclopropyl, cyclopentyl, cyclohexyl, which are optionally substituted by identical or different substituents from the group consisting of fluorine, chlorine, bromine, iodine, cyano, nitro, and a straight chain or branched alkyl having up to 5 carbon atoms, denote straight chain or branched alkyl, alkenyl or acyl each having up to 6 carbon atoms, or denote phenyl, which is optionally monosubstituted to disubstituted by identical or different substituents from group consisting of nitro, fluorine, chlorine, bromine, iodine, carboxyl and straight chain or branched alkoxycarbonyl having up to 5 carbon atoms, or R$^3$ denotes benzyl, acetyl or straight chain or branched alkoxycarbonyl having up to 4 carbon atoms, denotes straight chain or branched alkyl having up to 6 carbon atoms, which is substituted by carboxyl, hydroxyl, straight chain or branched acyl or alkoxycarbonyl each having up to 4 carbon atoms, phenoxyl, benzoyl which are optionally substituted by fluorine, chlorine, bromine, cyano, nitro or by straight chain or branched alkyl having up to 4 carbon atoms, or R$^5$ denotes a group of a formula —SO$_2$—R$^{14}$, in which R$^{14}$ denotes phenyl, trifluoromethyl or straight chain or branched alkyl having up to 3 carbon atoms, a denotes a number 0, 1 or 2, b denotes a number 0 or 1, R$^7$ denotes hydrogen or a straight chain or branched alkyl having up to 3 carbon atoms, R$^{13}$ denotes phenyl, trifluormethyl or straight chain or branched alkyl having up to 3 carbon atoms, R$^1$ represents hydrogen, straight chain or branched alkyl having up to 4 carbon atoms, tert.butoxycarbonyl or a group of the formula —CO—R$^{15}$ in which R$^{15}$ denotes hydroxyl, straight chain or branched alkoxycarbonyl having up to 4 carbon atoms, cyclopentyl, cyclohexyl, or straight chain or branched alkyl having up to 5 carbon atoms, which is optionally substituted by fluorine, chlorine, bromine, carboxyl or straight chain or branched alkoxycarbonyl having up to 4 carbon atoms, or denotes phenyl, which is optionally substituted by hydroxyl, carboxyl or straight chain or branched alkoxy or alkoxycarbonyl each having up to 4 carbon atoms, L represents an oxygen or sulfur atom, R$^2$ and R$^3$ are identical or different and represent hydrogen, cyclobutyl, cyclopentyl, cyclohexyl or straight chain or branched alkyl, alkoxycarbonyl or alkenyl each having up to 6 carbon atoms, or represent benzoyl or phenyl, which are optionally monosubstituted to trisubstituted by identical or different substituents from the group consisting of fluorine, chlorine, bromine, iodine, carboxyl, cyano, nitro and a straight chain or branched alkyl, alkoxy or alkoxycarbonyl each having up to 5 carbon atoms, and R⁴ represents phenyl, which is optionally monosubstituted to trisubstituted by identical or different substituents from the group consisting of hydroxyl, cyclopentyl, cyclohexyl; fluorine, chlorine, bromine, iodine, intro, trifluoromethyl, difluoromethyl, cyano, carboxyl, and straight chain or branched alkyl, alkoxy, alkoxycarbonyl or acyl each having up to 6 carbon atoms, or phenyl is optionally substituted by phenyl, which is optionally monosubstituted to disubstituted by fluorine, chlorine or bromine, or a salt thereof.

3. The N-(3-benzofuranyl)urea-derivative of the formula according to claim 1,
in which A and D are identical or different and represent hydrogen, straight chain or branched acyl or alkoxycarbonyl each having up to 4 carbon atoms, or straight chain or branched alkyl having up to 3 carbon atoms, which is optionally substituted by carboxyl or alkoxycarbonyl having up to 4 carbon atoms, phenoxy or benzoyl, or represent fluorine, chlorine, bromine, nitro, cyano, trifluoromethyl, trifluoromethoxy, or a group of a formula —OR⁵, —S(O)ₐR⁶, —(O—CH₂CO)ᵦ—NR⁷R⁸, —CO—NR⁹R¹⁰, —SO₂—NR¹¹R¹² or —NH—SO₂R¹³,
in which R⁵, R⁶, R⁸, R⁹, R¹⁰, R¹¹ and R¹² are identical and denote hydrogen, cyclopropyl, cyclopentyl, or cyclohexyl, which are optionally substituted by identical or different substitutents from the group consisting of fluorine, chlorine, bromine, iodine, cyano, nitro and a straight chain or branched alkyl having up to 3 carbon atoms,
denote straight chain or branched alkyl, alkenyl or acyl each having up to 3 carbon atoms, or
denote phenyl, which is optionally monosubstituted to disubstituted by identical or different substituents from the group consisting of nitro, fluorine, chlorine, bromine, iodine, carboxyl and straight chain or branched alkoxycarbonyl having up to 3 carbon atoms,
or R⁵ denotes benzyl, acetyl or straight chain or branched alkoxycarbonyl having up to 3 carbon atoms, denotes straight chain or branched alkyl having up to 4 carbon atoms, which is substituted by carboxyl, hydroxyl, straight chain or branched acyl or alkoxycarbonyl each having up to 3 carbon atoms, phenoxy, or benzoyl,
or R⁵ denotes a group of a formula —SO₂—R¹⁴,
in which R¹⁴ denotes phenyl, trifluoromethyl or methyl,
a denotes a number 0, 1 or 2,
b denotes a number 0 or 1,
R⁷ denotes hydrogen, methyl or ethyl,
R¹³ denotes phenyl, trifluoromethyl or methyl, R¹ represents hydrogen or straight chain or branched alkyl having up to 3 carbon atoms or a group of the formula —CO—R¹⁵,
in which R¹⁵ denotes hydroxyl, straight chain or branched alkoxycarbonyl having up to 3 carbon atoms, cyclopentyl, cyclohexyl, or straight chain or branched alkyl having up to 4 carbon atoms, which is optionally substituted by fluorine, chlorine, bromine, carboxyl or straight chain or branched alkoxycarbonyl having up to 3 carbon atoms, or denotes phenyl, which is optionally substituted by hydroxyl, carboxyl or straight chain or branched alkoxy or alkoxycarbonyl each having up to 3 carbon atoms, L represents an oxygen or sulfur atom, R² and R³ are identical or different and represent hydrogen, cyclobutyl, cyclopentyl, cyclohexyl or straight chain or branched alkyl, alkoxycarbonyl or alkenyl each having up to 5 carbon atoms, or represent benzoyl or phenyl, which are optionally monosubstituted to tri substituted by identical or different substituents from the group consisting of fluorine, chlorine, bromine, iodine, carboxy, cyano, nitro and a straight chain or branched alkyl, alkoxy or alkoxycarbonyl each having up to 3 carbon atoms, and R⁴ represents phenyl, which is optionally monosubstituted to trisubstituted by identical or different substituents from the group consisting of hydroxyl, cyclopentyl, cyclohexyl, fluorine, chlorine, bromine, nitro, trifluoromethyl, difluoromethyl, cyano, carboxyl, straight chain or branched alkyl, alkoxy, alkoxycarbonyl or acyl each having up to 5 carbon atoms, and phenyl is optionally substituted by phenyl, which is optionally monosubstituted to disubstituted by chlorine, or a salt thereof.

4. The N-(3-benzofuranyl)urea-derivative according to claim 1 wherein such compound is N-[2-(2',4'-dichlorobenzoyl)-6-methoxy-benzofuran-3-yl]urea of the formula

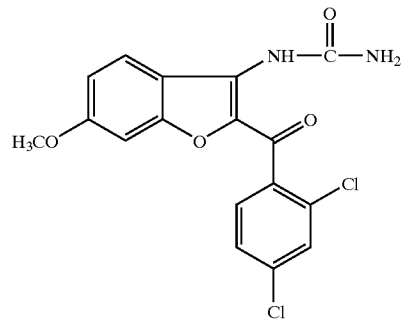

or a salt thereof.

5. The N-(3-benzofuranyl)urea-derivative according to claim 1 wherein such compound is N-[3-(6-methoxy-2-(2',4'-dimethyl-benzoyl)] benzofuranyl)urea of the formula

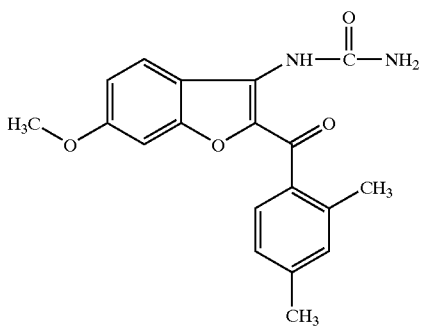

or a salt thereof.

6. The N-(3-benzofuranyl)urea-derivative according to claim 1 wherein such compound is N-[2-(2', 4'-dichlorobenzoyl)-6-nitro-benzofuran-3yl]urea of the formula

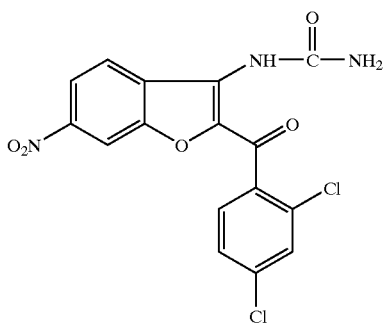

or a salt thereof.

7. The N-(3-benzofuranyl)urea-derivative according to claim 1 wherein such compound is [2-(2,4-dichlorobenzoyl)-3-ureido-benzofuran-6-yloxy] acetic acid methyl ester of the formula

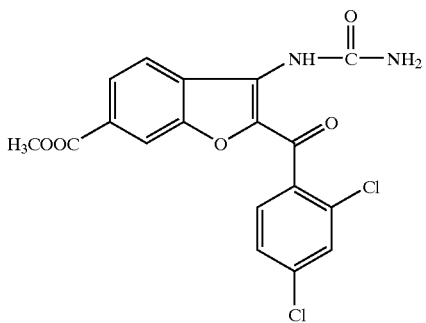

or a salt thereof.

8. The N-(3-benzofuranyl)urea-derivative according to claim 1 wherein such compound is methansulfonic acid 2-(2, 4-dichloro-benzoyl)-3-benzofuran-6 yl-ester of the formula

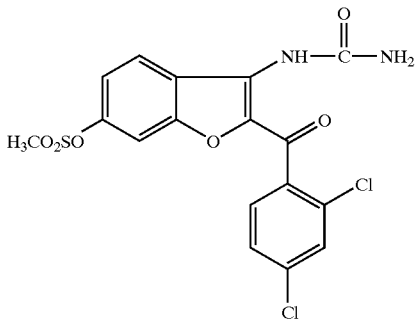

or a salt thereof.

9. A composition for the treatment of acute and chronic inflammatory processes comprising an amount effective therefor of a compound or salt thereof according to claim 1 and a pharmacologically acceptable diluent.

10. A method of treating acute and chronic inflammatory processes in a patient in need thereof which comprises administering to such patient an amount effective therefor of a compound or salt thereof according to claim 1.

11. The N-(3-benzofuranyl)urea-derivative according to claim 1 wherein such compound is N-[2-(2', 4'-dichlorobenzoyl)-6-hydroxy-benzofuran-3-yl]urea of the formula

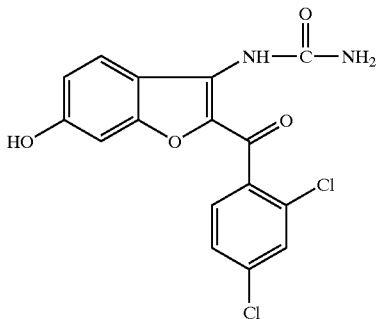

or a salt thereof.

* * * * *

UNITED STATES PATENT AND TRADEMARK OFFICE
CERTIFICATE OF CORRECTION

PATENT NO.    : 6,677,372 B2
DATED         : January 13, 2004
INVENTOR(S)   : Braunlich et al.

It is certified that error appears in the above-identified patent and that said Letters Patent is hereby corrected as shown below:

Column 10,
Lines 4 and 5, " $\dfrac{[1-((R_x-R_b))]}{((R_o-R_b))} \cdot 100$ " should read -- $\dfrac{[1-((R_x-R_b))]}{((R_o-R_b))} \cdot 100$ --

Columns 35 and 36,
Table 2 – continued, should read

| 25 | OCH₃ | O | H | H | 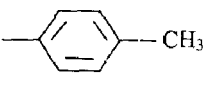 | 50.4 | 222 | 0.33 (I) |
| 26 | OCH₃ | O | H | H | 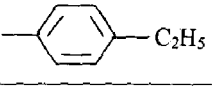 | 9 | 217 | 0.36 (I) |
| 27 | OCH₃ | O | H | H | 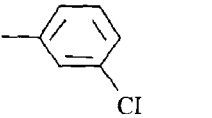 | 33.5 | 214 | 0.4 (I) |

Column 45,
Line 47, "$R^{10}$, $R^{10}$ and" should read -- and $R^{10}$, $R^{11}$ and --

Column 47,
Line 42, "and $R^5$ and" should read -- and $R^8$ and --

Column 48,
Line 18, "$R^3$ denotes" should read -- $R^5$ denotes --

UNITED STATES PATENT AND TRADEMARK OFFICE
CERTIFICATE OF CORRECTION

PATENT NO. : 6,677,372 B2
DATED : January 13, 2004
INVENTOR(S) : Braunlich et al.

It is certified that error appears in the above-identified patent and that said Letters Patent is hereby corrected as shown below:

<u>Column 48 (cont'd),</u>
Line 39, "trifluormethyl" should read -- trifluoromethyl --

Signed and Sealed this

Third Day of May, 2005

JON W. DUDAS
*Director of the United States Patent and Trademark Office*